United States Patent
Machado Da Silva et al.

(10) Patent No.: US 10,018,528 B2
(45) Date of Patent: Jul. 10, 2018

(54) METHOD AND DEVICE FOR TESTING THE TIGHTNESS OF CORK STOPPERS

(71) Applicant: AMORIM CORK RESEARCH & SERVICES, LDA, Mozelos VFR (PT)

(72) Inventors: Luis Filipe Peixoto Machado Da Silva, Mozelos (PT); Nuno Duarte de Figueiredo Seabra Amador, Espinho (PT)

(73) Assignee: AMORIM CORK RESEARCH & SERVICES, LDA, Mozelos (PT)

( * ) Notice: Subject to any disclaimer, the term of this patent is extended or adjusted under 35 U.S.C. 154(b) by 179 days.

(21) Appl. No.: 15/112,418

(22) PCT Filed: Jan. 16, 2015

(86) PCT No.: PCT/PT2015/000004
§ 371 (c)(1),
(2) Date: Jul. 18, 2016

(87) PCT Pub. No.: WO2015/108431
PCT Pub. Date: Jul. 23, 2015

(65) Prior Publication Data
US 2016/0334299 A1 Nov. 17, 2016

(30) Foreign Application Priority Data
Jan. 17, 2014 (PT) .......................... 107408

(51) Int. Cl.
*G01M 3/26* (2006.01)
(52) U.S. Cl.
CPC .................... *G01M 3/26* (2013.01)
(58) Field of Classification Search
CPC .................. G01M 3/00; G01M 3/26
See application file for complete search history.

(56) References Cited

U.S. PATENT DOCUMENTS

| 4,037,724 A * | 7/1977 | Schultz ............... B07C 5/34 209/587 |
| 2011/0127432 A1 * | 6/2011 | Federici ............ G01N 21/3581 250/339.07 |

FOREIGN PATENT DOCUMENTS

FR 2727519 A1 * 5/1996 ............. G01N 19/02

OTHER PUBLICATIONS

David P. Faria, et al. "Permeability of Cork to Gases", Journal of Agriculture and Food Chemistry, American Chemical Society, US., vol. 59, No. 8, Aug. 1, 2011.

* cited by examiner

*Primary Examiner* — Nguyen Ha
(74) *Attorney, Agent, or Firm* — Porzio Bromberg & Newman P.C.

(57) ABSTRACT

The present invention relates to a process and a device (1) to test the sealing of cork stoppers (R). The device (1) comprises a partitioning mechanism dividing a chamber in two compartments (8a, 8b). The partitioning mechanism comprises: an adjustable insulator (9) configured to hermetically seal a central part of the stopper (R) from the outside environment and simultaneously to arrange each end of the stopper (R) in one of the compartments (8a, 8b); and an insulator actuation member (10) to arrange the insulator (9) on the central part of the stopper (R). The device farther comprises a block (11a) for closing the compartment (8a); an inlet (12) connected to a test fluid source, the source arranged in the block (11a), and a detection member (13) connected to the same block (11a). The present invention finds application in the field of cork stopper production and in the cork industry in general.

15 Claims, 8 Drawing Sheets

METHOD AND DEVICE FOR TESTING THE TIGHTNESS OF CORK STOPPERS

FIELD OF THE INVENTION

The present invention relates to a process and a device to test the sealing of cork stoppers, in order to improve selection reliability of stoppers that are effectively suited to perform the sealing function, in particular for the case of sealing of wine bottles. The present invention finds application in the field of cork stopper production and in the cork industry in general.

BACKGROUND OF THE INVENTION

The use of corks stoppers for retention and sealing of liquids in containers is well known since ancient times. In particular, cork stoppers are preferably used in wine bottles or other alcoholic beverages.

The wide use of corks stoppers to close and seal wine containers and other alcoholic beverages is due mainly to the specific characteristics of cork, such as its elasticity and compressibility. The cellular structure of cork provides the sealing of containers having wine, in order to allow the wine to nurture harmoniously inside the container. This is of outmost importance as it is directly related with the organoleptic characteristics of the wine.

The insulation from the outside environment of the bottle is one of the crucial factors for the appropriate development of a wine, particularly still wine, as it is necessary to prevent contaminations and owners infiltrations, which in excessive levels modifies the wine composition. Therefore, oxygen is frequently responsible for wine deterioration. Obviously, it is also essential to prevent leakage of wine when the bottle is horizontally stored. Thus, seating of stoppers is a crucial element in the selection of appropriate stoppers One of the major problems that cork stopper producers face these clays is the lack of means for precise measurement of the sealing ability of cork stoppers, allowing carrying out an individual selection, totally reliable, of the cork stoppers that provide a sealing ability in accordance with an objective criterion.

It is known that the problems associated with poor sealing of a container are caused by defects on the surface and inside the body of the cork stopper.

In the contest of the present invention, it should be pointed out the defect named "wormhole" ("bicho") in the art. This defect is recognized by the person skilled in the art due to the presence of holes and/or channels made by ants or other insects during the natural development phase of cork on the cork oak.

The sealing ability of a stopper is compromised when said channels extend between both end faces (also designated extremities) of the stopper or between the areas of the stopper body near and contiguous to these faces. In these cases, a liquid and/or gas communication is established between the end part of the stopper that is inside the bottle neck and the opposing end part of the same stopper that is facing the outside of the bottle neck. This fluid communication is responsible for early deterioration or even leakage of the liquid stored in the bottle.

More specifically, there is in the art a lack of technical means for checking out precisely if there are communicating channels between the plurality of non-communicating holes and/or channels usually present in a cork stopper, wherein, in many cases, these holes/channels are not even noticeable for the human operator.

To circumvent this problem, the persons skilled in the art have used accessory techniques that aim to increase the reliability level of the sealing ability of the stoppers. Examples of the above mentioned are the arrangement of cork disks at the stopper end which lays inside the bottle; colmatation of cork stopper; and arranging aluminium covers on the outside of the bottle neck. However, these techniques do not assure the intended result and in addition increase the general costs of the stopper production process.

Therefore, the current attempts to solve insufficient sealing of the cork stoppers, yield direct and indirect costs and impart significant resource consuming.

Several processes which can be used at the industrial level have been developed over the years in order to select cork stoppers having a better ability for sealing containers, namely bottles of still and sparkling wine.

Traditionally, the selection of cork stoppers is carried out through visual inspection by specialized technicians. These technicians look for defects, such as those mentioned above and others, on the surface of the inspected cork body that can be interpreted as potential compromisers of the sealing ability. This analysis can also take place directly in cork boards from which corks stoppers are obtained. In this way, after visual inspection, the cork stoppers are classified in different quality classes and the cork boards are approved for production of cork stoppers or discarded for other applications.

Understandably, the visual process by human operators for the assessment of the structural integrity of cork stoppers, in order to predict its sealing behaviour, is an empirical not reliable process, although the substantial experience held by the specialized technicians.

In order to make the process of visual inspection of the outside surface of cork stoppers more efficient and faster, several automatic processes and systems have been developed over the years. One of these processes is described in patent application PT 103749. In this application an automatic method and system of quality control of corks stoppers comprising means for capturing images using visible radiation of the outside surfaces of cork stoppers is disclosed. The obtained images are compared with predefined parameters in order to classify the stoppers according with the presence of defects.

These processes comprising surface inspection of the cork stoppers, even very extensive, have considerable unreliability associated therein, as they do not take into account the internal structure of the cork stoppers.

In order to complement the visual inspection of cork stoppers, processes to analyse their internal structure had been developed. One of these processes is described in the recent patent application PT 104902, which discloses a "Non-destructive and non-invasive method for inspection of plant materials based on the use of electromagnetic radiation". This method comprises a non-invasive and non-destructive monitoring (using electromagnetic radiation) of internal parameters of natural cork stoppers (such as areas of a stopper with different densities) and subsequent storage of data collected in this monitoring process in a database. The collected data are then used to create a correlation between cork defects and permeability to gases, namely, oxygen. In other words, it is a prediction method of the sealing ability of cork stoppers and, as such, it requires time to create a well defined correlation. Nevertheless it only provides a prediction of the sealing ability.

This type of processes allows correlating the permeability to oxygen with the presence of defects inside of a cork stopper, taking also into account the internal structure of the stopper. However, they are confined to an estimation of the sealing ability of a cork stopper, not providing precise data for each individual cork stopper.

Therefore, both the merely superficial (visual) analyses and the analyses that take into account the internal structure of cork stoppers do not produce precise results when each cork stopper is taken individually. In fact, tests carried out by the process of the present invention have noticed a deficient sealing in cork stoppers considered suitable by the mentioned processes and vice versa, as it is hereinafter demonstrated in the present description.

On the other hand, the practical experience of wine producers and consumers and cork stopper producers has shown the existence of countless cases of deterioration of bottled wine, or even leakage of wine, when such incidents would not be expected nor desirable. These situations unequivocally show that, despite the efforts made by the cork industry, sealing deficiencies still persist that require resolution.

Accordingly, there is a need for an efficient process and device that can be industrially applied, that provide a real and objective measurement of the sealing ability of each tested cork stopper, in order to eliminate the deficiencies of statistics and visual analysis ascribable to the processes and systems of the prior art and, therefore, to contribute for a truly significant effectiveness in the selection of cork stoppers.

SUMMARY OF THE INVENTION

A sealing test device (1) for checking out the sealing of a cork stopper (R), which cork stopper (R) comprises a body defining a central part (4) and two ends (5a, 5b), the device comprising:
- a cork stopper receiving chamber (7);
- a chamber partitioning mechanism, which divides the chamber (7) in two compartments (8a, 8b), the mechanism comprising:
  - an adjustable insulator (9) to said central part (4) of the cork stopper (R), wherein the insulator (9) is configured for, upon actuation, sealing hermetically the central part (4) of the cork stopper body in relation to the outside environment, and simultaneously for arranging each end (5a, 5b) of the stopper (R) in one of said compartments (8a, 8b).
  - an insulator actuation member (10), configured for, upon actuation, arranging the insulator (9) on the central part (4) of the cork stopper body;
- at least one chamber compartment closing block (11a, 11b) arranged for, in operation, closing and hermetically isolating a respective compartment (8a, 8b) in relation to the outside environment and, together with said insulator (9), for isolating hermetically the compartments (8a, 8b) from each other;
- at least one test fluid inlet (12) arranged in at least one closing block (11a, 11b);
- at least one detection member (13) arranged for detecting head loss or for detecting test fluid in at least one of the compartments (8a, 8b); and
- at least one test fluid source (14) connected to at least one test fluid inlet (12).

In one aspect of the invention, said insulator (9) is made of elastic and sealing material.

In another aspect, the insulator (9) is an inflatable sleeve and the actuation member (10) of the insulator is a compressor.

In a further aspect, the test fluid is a suitable gas for food industry as a food grade gas, and the test fluid source (14) is a compressor.

In another aspect, the detection member (13) is a pressure gauge or a flowmeter, preferably a manometer.

In a preferred embodiment of the invention, the device (1) comprises an inflatable sleeve made of elastic and sealing material; a compressor to inflate said inflatable sleeve; a test fluid inlet (12) arranged in a closing block (11a); a detection member (13) connected to the closing block (11a); and a compressor connected to the test fluid inlet (12).

In a preferred embodiment, the device (1) of the invention comprises a closing block (11a) and a closing block (11b) arranged for, in operation, closing and hermetically isolating the compliment (8a) and the compartment (8b), respectively.

The present invention further relates to a sealing test process for checking out the sealing of a cork stopper (R), the process comprising the steps of:
a) dividing the cork stopper (R) in two ends (5a, 5b) and a central part (4);
b) hermetically sealing the central part (4) of the cork stopper body in relation to the outside environment by means of an inflatable sleeve;
c) isolating the ends (5a, 5b) of the stopper (R) in compartments (8a, 8b);
d) closing, at least one of said compartments (8a, 8b), such that the at least one compartment (8a, 8b) thus closed is hermetically isolated from the outside environment;
e) pressurizing said at least one compartment (8a, 8b) with a test fluid;
f) detecting a head loss in said at least one closed compartment (8a, 8b) or detecting the presence or absence of test fluid in the opposing compartment (8b, 8a).

In one embodiment of the process of the invention, in said step d), both compartments (8a, 8b) are closed so as to hermetically isolate them from the outside environment. In this case, steps e) and f) are preferably repeated alternately for each of the compartments (8a, 8b).

In one aspect of the process of the invention, in step a) of dividing the cork stopper (R), the central part (4) has a size in the range of 5 to 30 mm, preferably has a size of 12 mm.

In another aspect of the process of the invention, step e) is carried oat with a pressure in the range of 150 to 1000 mbar, for 0.4 to 10 seconds, preferably 500 mbar for 1 to 2 seconds, more preferably with a pressure of 900 mbar for 0.4 to 0.5 seconds.

BRIEF DESCRIPTION OF THE DRAWINGS

The present invention will become more apparent by the following detailed description with reference to the attached, drawings, in which.

DETAILED DESCRIPTION OF THE INVENTION

The present invention relates to a process and device for checking out the sealing ability of corks stoppers in containers of food products, namely wine bottles. This invention provides a reliable way of selecting appropriate cork stoppers, based on actual assessment of the sealing ability of each cork stopper submitted to the test.

In the present application, the use of the term "and/or" is intended to mean that both conditions are true or only one is true. For example, the term "holes and/or channels", means "holes and channels or holes or channels".

In the context of the present description, the term "comprising" must be understood as "including, among others". As such, said term should not be interpreted as "consisting only of".

Any X value shown throughout the present description must be interpreted as an approximate value of the true X value, as such approximation to the true value would reasonably be expected by the skilled artisan due the experimental conditions and/or measurements that produce deviations from the true value.

Unless otherwise mentioned, ranges of values shown in the present description provide a simplified and technically accepted way to show each individual value within, the respective range. As an example, the term "1 to 2" or "between 1 and 2" means any value within this interval, for example 1.0; 1.1; 1.2; 1.3; 1.4; 1.5; 1.6; 1.7; 1.8; 1.9; 2.0. All values mentioned in the present description must be interpreted as approximate values, as specified above. For example, "2.3" means "about 2.3".

The process and device herein described can be used to test the sealing ability of any type of cork stopper.

The sealing test device of the invention allows to apply the sealing test process, in order to use it in all cork stoppers (R) produced in an industrial production process, so as to assess objectively and individually the sealing ability of each cork stopper (R) produced.

In the context of the present invention, the term "cork stopper" relates to stoppers made of natural cork, colmated natural cork, agglomerated cork, micro-agglomerated cork, technical cork or the like and combinations thereof.

The term "natural cork stopper" or "natural stopper" relates to a stopper (R) comprising a body formed only of natural cork.

The term "colmated natural cork stopper" or "colmated cork stopper" relates to natural cork stoppers with its pores colmated with cork powder.

The term, "agglomerated cork stopper" or "agglomerated stopper" relates to a stopper (R) comprising a body made of agglomerated cork with a particle size higher than 2 mm.

The term "micro-agglomerated cork" relates to agglomerated cork with cork grains having a particle size of 0.1-2 mm.

The term "micro-agglomerated cork stopper" or "micro-agglomerated stopper" relates to a stopper (R) comprising a body formed with micro-agglomerated cork.

Figure 3:
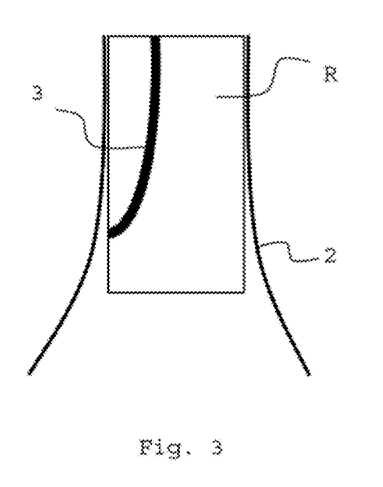
FIG. 3 schematically illustrates a section view of a stopper inserted in a bottle, showing the presence of a communicating internal channel.
Figure 4:
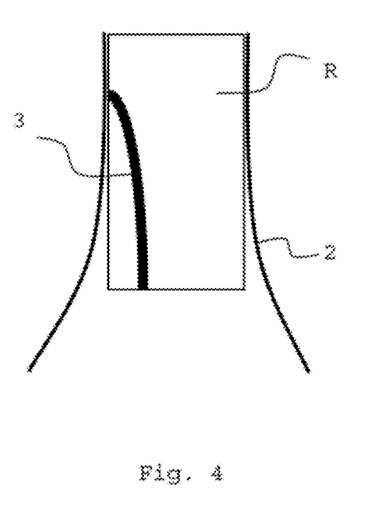
FIG. 4 schematically illustrates a section view of the same cork shown in FIG. 3 but inserted up-side-down in the bottle, showing its internal channel that is no longer communicating in this case.

The term "cork stopper body", or simply "body", relates to the part of the stopper (R) that is inserted in the neck (2) of a bottle, up to the external limit of the bottle neck (2) end, after the corking process (see example in FIGS. 3 and 4). This is the part of the stopper (R) that closes and/or seals the bottle when the stopper (R) is inserted. Unless otherwise mentioned, the shape of a stopper (R) body is substantially cylindrical or conical, notwithstanding they can be chamfered or rounded in its insertion end.

Figure 1:
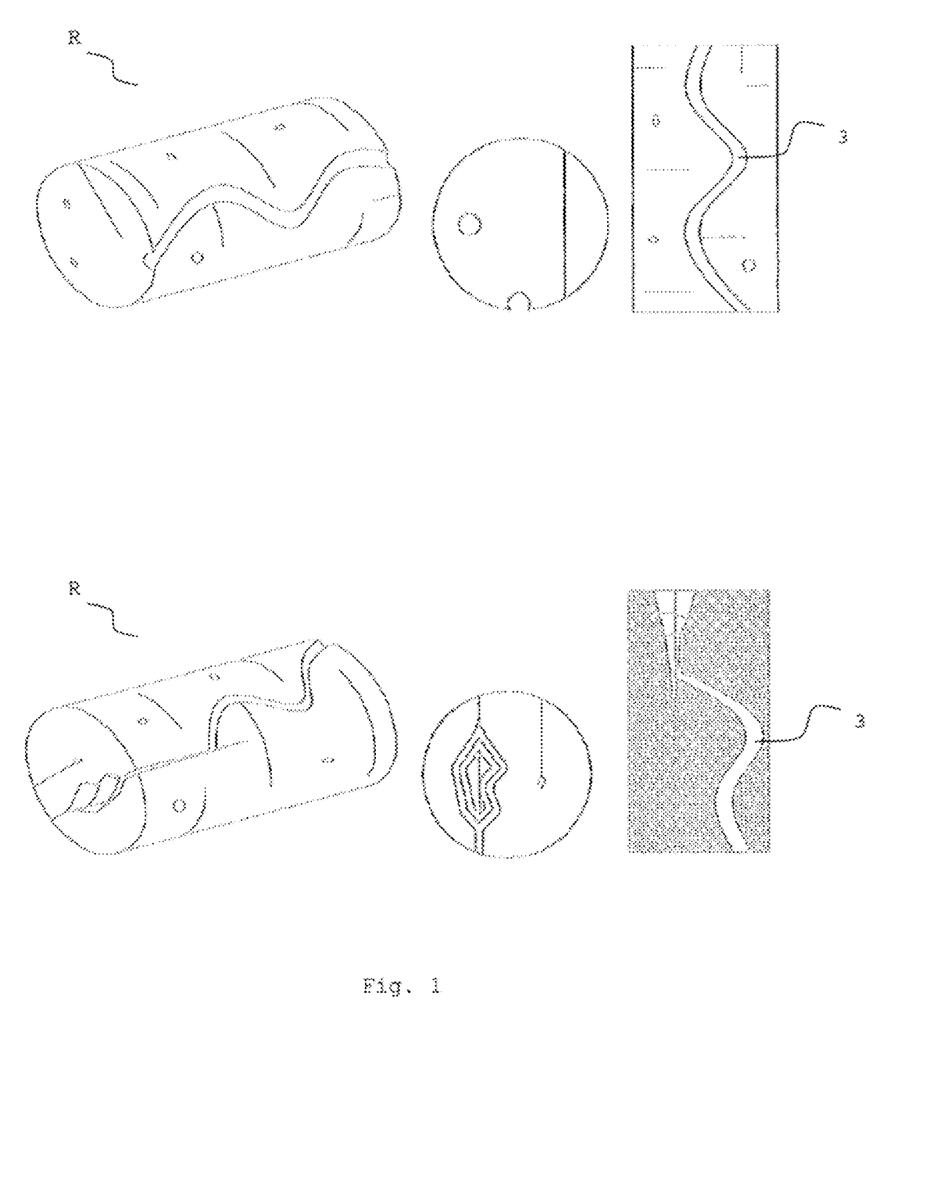
FIG. 1 schematically represents two cork stoppers having a defect ("bug") and respective top and cross-sectional views, showing communicating internal channels.

The term "communicating channel" relates to a defect (3) internally present in the cork stopper (R) body, that allows fluid communication between the inside and the outside of the bottle. Examples of defects (3) construed as communicating channels can be observed in FIGS. 1 and 3. An example of a defect (3) that it is not a communicating channel can be observed in FIG. 4.

The term "fluid communication" relates to a communication or passage way of a liquid and/or gas between, at least, two points.

The term "normalized bottle neck" relates to bottle necks (2) having diameters in the range of about 16.5 to 18.5 mm.

The term "sparkling wines" relates to wines having a certain dose of carbon dioxide to make lasting bubbles.

The term "still wine" relates to white, red or rose wines that are not sparkling wines, nor spirits.

The term "wine" relates to still wines and sparkling wines, unless otherwise specified.

The terra "organoleptic characteristic" relates to colour, aroma and flavour characteristics of a wine.

The invention will be hereinafter explained with non-limiting reference to the attached drawings and mentioning cork stoppers (R) to seal bottles having wine, as this is the preferred aim of the invention. However, the invention could be used to test the sealing of any cork stopper (R) regardless the type of container and its content, which can be solid, liquid and/or gas.

The process and device of the present invention allow to objectively checking out the sealing of a cork stopper (R), by means of a test briefly comprising:

division of the stopper (R) body into three distinct parts, a central part (4) and two ends (5a, 5b) of the body; and     insulation of said ends (5a, 5b) in respective compartments (8a, 8b), in order to pressurize a compartment (8a) with a test fluid and checking if any passage of this fluid took place through the interior of the stopper (R) to the non-pressurized opposing compartment (8b).

The detailed description of the process for checking the sealing of the present invention is hereinafter described.

Figure 2:
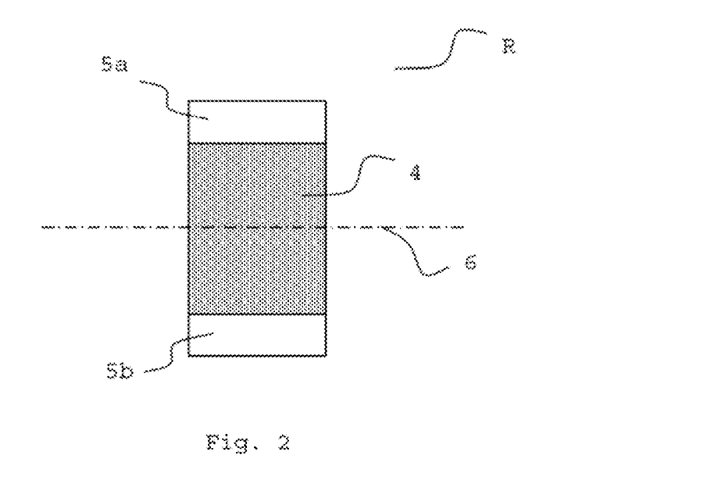
FIG. 2 schematically illustrates the front view of a cork stopper, showing a central axis, the central part and both ends of the cork stopper body.

In the context of the present description, with reference to FIG. 2, the term "central part of the cork stopper" or "central part" relates to a surface area (4) defined around the body of the stopper (R), that can be assessed in a simple way from a transverse central axis (6) (axis perpendicular to the length of the stopper (R), the length of the stopper being measured from one end face of the stopper to the other end face thereof) that divides the stopper body into two equal halves (see FIG. 2).

In the present invention, the central part (4) can have a size in the range of 5 to 30 mm in length.

For better understanding and by way of example, if the central part (4) has a length of 5 mm, such central part (4) corresponds to all surface area of the stopper body delimited by a reference extension of 5 mm in length, the reference extension of which is obtained from a measurement of 2.5 mm for each side of said central axis (6) of the stopper (R). Thus, see FIG. 2, the central part (4) of the stopper (R) of FIG. 2 corresponds to the designated dark area (extending around all surface of fee stopper), said reference extension being measured for each side of the axis (6), corresponding to the height between the two horizontal limits of the dark area.

Preferably, the central part (4) has a size between 8 and 20 mm, more preferably between 10 and 16 mm and particularly preferably has 12 mm, in length.

Still referring to FIG. 2, the ends (5a, 5b) of a stopper body designate both parts of the stopper (R) complementary to the central part (4), in other words, the two parts (5a, 5b) of the stopper (R) comprised between the limits of the central part (4) and the faces of the stopper (R), including said faces. As can be seen in FIG. 2, the ends (5a, 5b) of the stopper (R) are separated by the central part (4) thereof.

More specifically, with reference to FIG. 5 to 9, the present invention relates to a device (I) for checking out the sealing of cork stoppers (R), wherein the cork stopper (R) comprises a body defining a central part (4) and two ends (5a, 5b), such as defined above.

The sealing test device (1) of the invention comprises:
a cork stopper receiving chamber (7);
a chamber partitioning mechanism which divides the chamber (7) in two compartments (8a, 8b), wherein said partitioning mechanism comprises:
  an adjustable insulator (9) to said central part (4) of the cork stopper (R), wherein the insulator (9) is configured for, upon actuation, sealing hermetically the central part (4) of the cork stopper body in relation to the outside environment, and simultaneously for arranging each end (5a, 5b) of the stopper (R) in one of said compartments (8a, 8b),
  an actuation member (10) of the insulator (9), configured for, upon actuation, arranging the insulator (9) on the central part (4) of the cork stopper body;
at least one chamber compartment closing block (11a, 11b) arranged for, in operation, closing and hermetically isolating a respective compartment (8a, 8b) in relation to the outside environment and, together with said insulator (9), for isolating hermetically the compartments (8a, 8b) from each other;
at least one test fluid inlet (12) arranged in at least one closing block (11a, 11b);
at least one detection member (13) arranged for detecting head loss or for detecting test fluid in at least one of the compartments (8a, 8b); and
at least one test fluid source (14) connected to at least one test fluid inlet (12).

Figure 5:
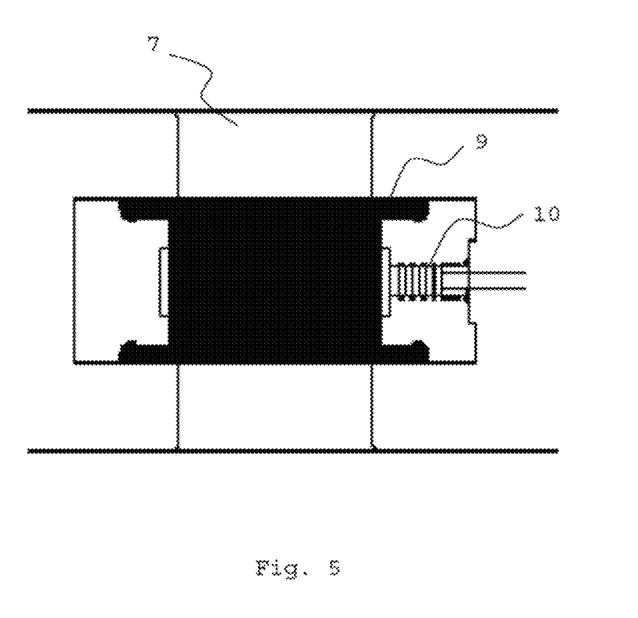
FIG. 5 schematically shows the device of the invention without closing blocks nor the cork stopper arranged in the receiving chamber, showing distinctively the insulator.
Figure 6:
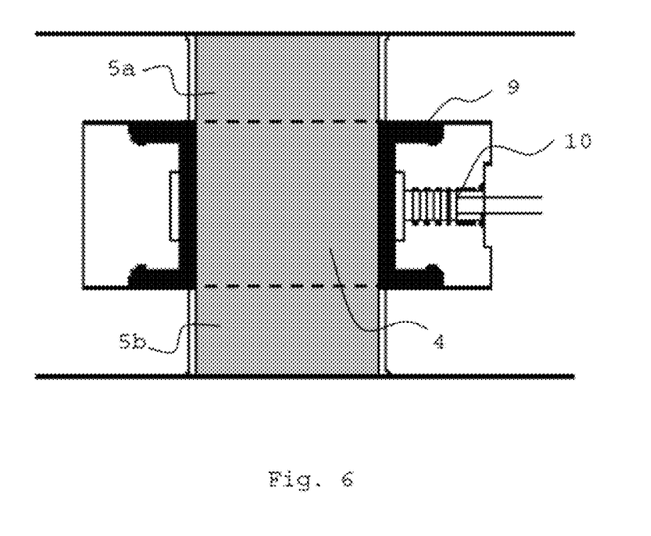
FIG. 6 illustrates a cork stopper placed in the receiving chamber, allowing seeing the hermetic compartments.

The cork stopper receiving chamber (7) comprises a housing in which the cork stopper (R) to be tested is placed. This housing helps confining and positioning the cork stopper (R), so as to allow a correct actuation of the remaining members of the device (1). The chamber (7) can have a shape similar to the stopper (R) shape, generally cylindrical or conical, although this is not crucial as it largely depends on a great extent on the design and/or constructive options of the skilled person. In FIG. 5, an example of the receiving chamber (7) can be seen without any cork stopper (R) therein for better understanding, and in FIG. 6 to 9 a cork stopper (R) placed in the receiving chamber (7) can be seen.

Figure 7:
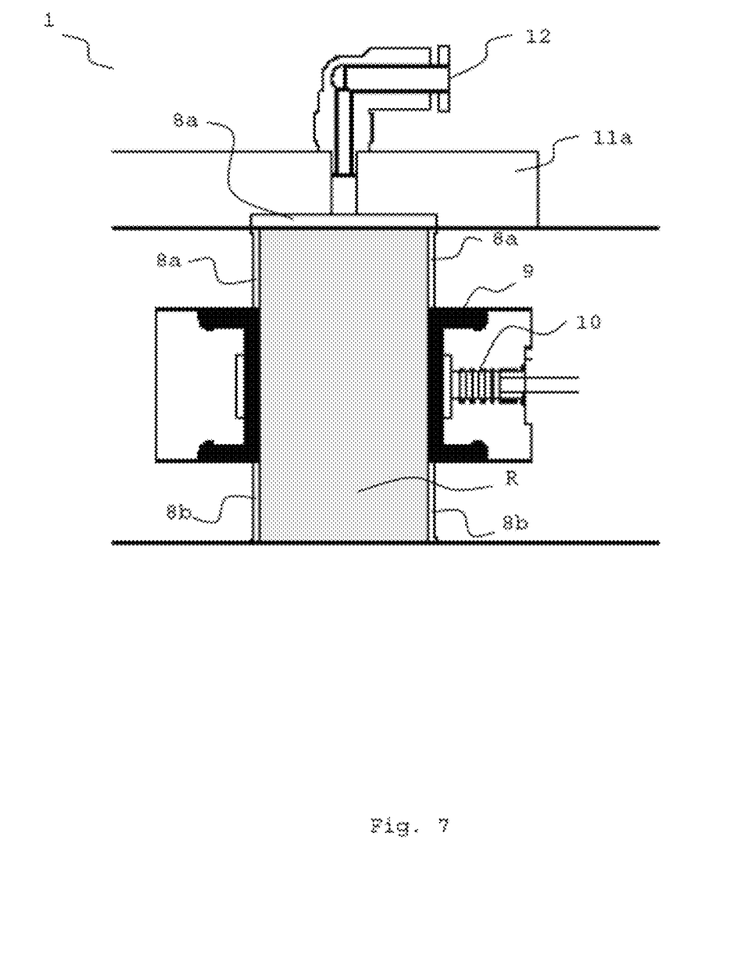
FIG. 7 schematically shows a device for checking out the sealing of the present invention with only one closing block.
Figure 8:
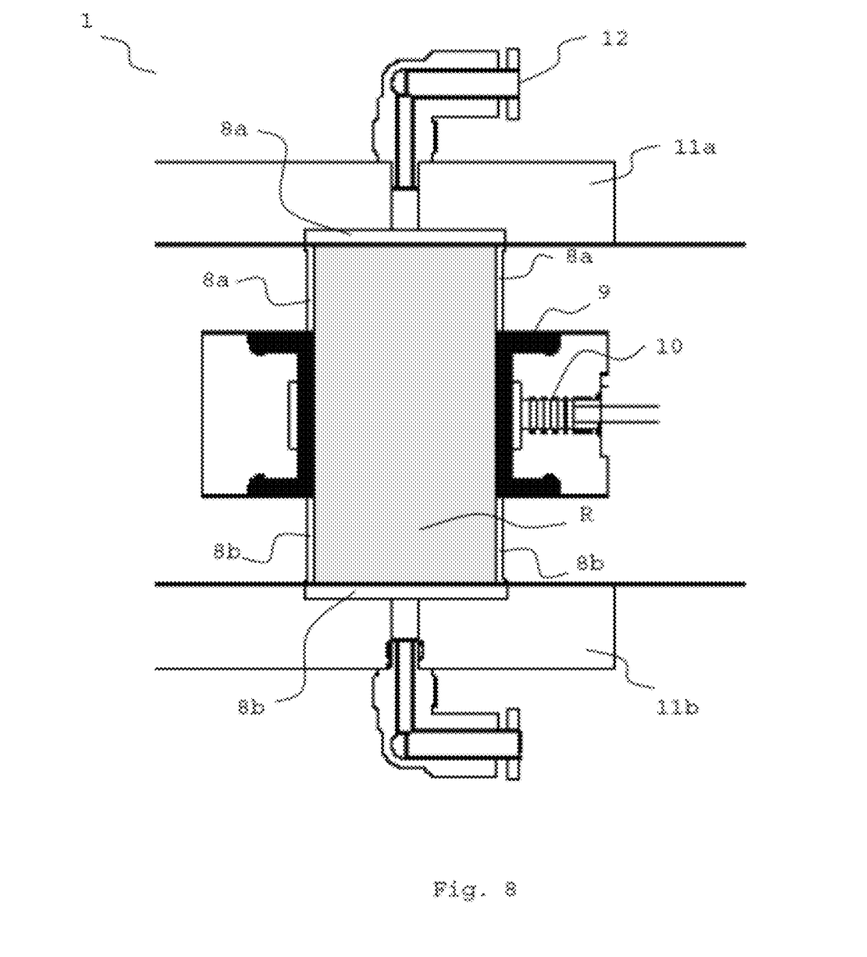
FIG. 8 is an embodiment of the invention showing two closing blocks in place.
Figure 9:
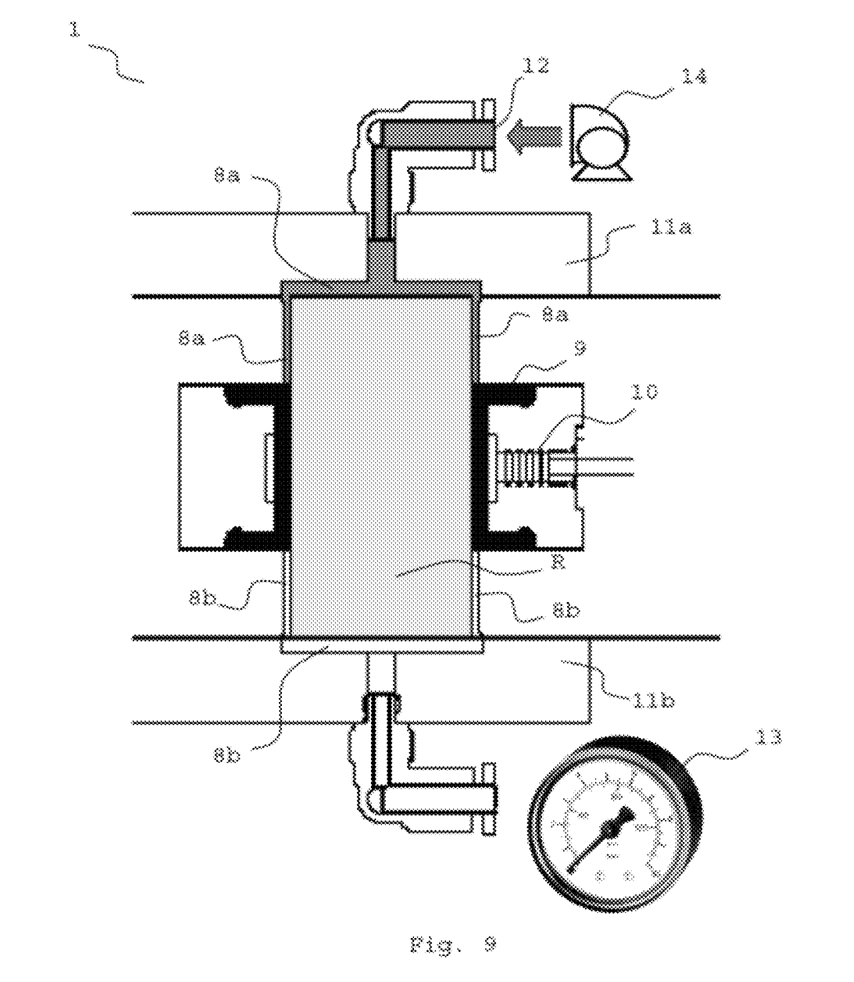
FIG. 9 illustrates the device of FIG. 8 in operation, with the top compartment pressurized with test fluid.

After placing the stopper (R) in the receiving chamber (7), the partitioning mechanism is actuated (see FIG. 6 to 9). This mechanism is configured to divide the receiving chamber (7) into two compartments (8a, 8b) that keep hermetically isolated from each other as soon as one of them is closed by the closing block (11a, 11b) (as can be seen in FIG. 7 to 9). In one embodiment of the invention, both compartments (8a, 8b) are closed by respective closing blocks (11a, 11b) and therefore both compartments (8a, 8b) are isolated from the outside environment.

The partitioning mechanism comprises an insulator (9), preferably made of sealing elastic material, that is intended to adhere to the central part (4) of the stopper (R) so as to cover the stopper in order to hermetically seal it in relation to the outside environment. On the other hand, this covering and sealing action of the central part (4) of the stopper further allows the separation of the receiving chamber (7) in two distinct compartments (8a, 8b). In the embodiment of FIG. 5, it can be seen that the insulator (9) surrounds the area of the receiving chamber (7) where the central part (4) of the stopper (R) will be placed.

In an embodiment, the insulator (9) is a membrane made of an inflatable and sealing material. In operation, the membrane is filled with a filling fluid by means of the insulator actuation member (10). More preferably, said membrane is an inflatable sleeve.

The insulator actuation member (10) can be, for example, a hydraulic or pneumatic actuator, such as a pump or a compressor.

In a preferred embodiment, the adjustable sleeve inflated by a compressor and firmly adheres to the wall of the cork stopper (R) on its central part (4) to provide sealing and, due to the volume increase of the sleeve by inflation, the sleeve also operates as a partition member, giving rise to two compartments (8a, 8b), hermetically separated from each other, one for each end (5a, 5b) of the cork stopper (R), as can be seen in FIG. 7 to 9.

After said partitioning, at least one closing block (11a, 11b) closes the respective compartment (8a, 8b), hermetically isolating it in relation to the outside environment and in relation to the non-closed compartment (8b, 8a), as shown in FIG. 7.

At this stage, the device (1) is prepared to proceed with the sealing test of the stopper (R). For this, a source (14) of test fluid is put into operation, preferably a compressor or a pump, in order to pressurize the compartment (8a, 8b) closed by said closing block (11a, 11b), wherein said closed compartment (8a, 8b) contains one of the ends (5a, 5b) of the stopper (R).

Obviously, if both compartments (8a, 8b) have been closed by blocks (11a, 11b), any of the compartments (8a, 8b) can be pressurized by the test fluid, as in this case both are hermetically isolated from the outside environment.

In FIG. 9, it is shown by way of example, the pressurized compartment (8a), filled with a darker colour than the opposing compartment (8b).

As both compartments (8a, 8b) are isolated from each other, the test fluid will only be able to communicate with the compartment (8b) opposed to the pressurized compartment (8a) if it passes through the interior of the body of the stopper (R). This situation will only take place if communicating defects, such as channels (3), exist in the interior of the stopper body, between the pressurized end (5a) and the non-pressurized end (5b) of the stopper (R).

The test fluid can be any fluid, liquid or gas, that is suitable for testing stoppers (R) of cork material. Preferably, the test fluid is a gas, as the main problem with the sealing of wine containers consists of oxygen infiltration through the cork stopper (R), deteriorating the organoleptic characteristics of the wine. On the other hand, the skilled person will understand that in case the cork stopper (R) does not allow a gas fluid to pass through the stopper, it is acceptable to conclude that same will apply to a liquid fluid, ensuring a complete sealing of the product to be sealed.

In this way, compressed air as test fluid or any other suitable gas that is compatible with the standards of the food industry and which does not damage the cork stoppers (R) can be used.

Still with reference to FIG. 9, after the fluid source (14) is put into operation, it is necessary to check out if there is fluid communication with the compartment (8b) opposed to the pressurized compartment (8a). For this, one can check if any head loss have taken place in the pressurized compartment (8a, 8b) or, in the case of the embodiment having two closing blocks (11a, 11b), one can check out if test fluid passed to the non-pressurized compartment (8b, 8a).

In this way, a detection member (13) arranged for detecting head loss or for detecting test fluid in at least one of the compartments (8a, 8b) will be necessary. This detection member (13) can be selected from the group comprising pressure gauges, pressure variation sensors and flowmeters. By way of example, the use of a manometer or flowmeter is suggested, although any other suitable instrument can be used depending on the industrial design implementation.

As to the operating parameters, it is necessary to assure an adhesive force of the insulator (9) to the central part (4) of the cork stopper body, so as to ensure the sealing of the stopper (in its central part (4)) in relation to the outside environment and the hermetic insulation between compartments (8a, 8b).

On the other hand, it is also necessary to take into account the pressure of the test fluid to be applied and its time of operation.

Tests have shown that a pressure of 2.3 bar for inflating a sleeve assure said adhesive force and other mentioned insulation requirements. However, the regulation of this parameter depends on the type of cork stopper, material of the sleeve and parameters related with the application of the test fluid, whereby they should be adjusted taking into account the particular industrial plant. This adjustment is may be carried out by the skilled person without further teaching.

With regard to the test fluid parameters, several tests have been carried out successfully, applying pressure values between 150 mbar and 1000 mbar in a range of operation time of 0.3 seconds to 10 seconds. Standard values for industrial application will be in the ranges of 300 to 600 mbar for 1 to 3 seconds, preferably 500 mbar for 1 to 2 seconds.

In a particularly preferred embodiment, a pressure of 900 mbar for 0.4 to 0.5 seconds is used.

Taking into account the nature of the test, higher values to those mentioned can obviously assure a well-succeed test, although in an industrial point of view they are uninteresting and moreover higher pressures can destroy the internal structure of the stopper (R), promoting, for example, the propagation of cracks or opening communicating channels that did not exist originally inside the stopper (R), or further breaking the hermetic sealing provided by the insulation sleeve between the compartments (8a, 8b).

Depending on the evaluation criteria, pressure values for the test fluid below 150 mbar can be used, although such option may experience implementation difficulties.

Independently of the above mentioned adequate pressure conditions of the test fluid, the skilled person will understand that such conditions are more severe than those experienced by the cork (R) in normal conditions of the stopper (R) inside the bottle neck (2), whereby the device (1) of the invention assures the reliability of the results in bottle.

In other words, a cork (R) that attests the sealing condition in the device (1) of the present invention, will be for sure appropriate to seal a container, as it will be additionally assisted by an insertion under pressure into the neck (2) at the time of corking, which will add a radial compression of the stopper (R) body and, in this way, a reduction in the size of putative internal channels (3) that might exist in the cork stopper.

In a preferred embodiment of the invention, the pressurization with test fluid is made sequentially in both compartments (8a, 8b) and the respective checking of fluid communication is carried out in the respective opposing compartments (8b, 8a). This option requires that both compartments (8a, 8b) are closed by closing blocks (11a, 11b).

The reason for this option is that, during the test, it is not possible to know which of the ends (5a, 5b) of the stopper (R) be placed inside the bottle neck (2). This question is relevant, as the cork (R) can seal in a certain direction (as in FIG. 4) but not in the opposing direction (as in FIG. 3). In other words, depending on the route followed by an eventual existing defect (3) (channel) inside the stopper body, such defect may allow a fluid communication from the outside to the inside of the bottle, but not allow it in the opposing direction. In these cases, if the test is made only in one direction, there is the risk of not detecting this possibility.

In this sense, the device (1) of the invention will have preferably a test fluid inlet (12) and a detection member (13) in each compartment (8a, 8b).

The present invention further relates to a process for checking out the sealing of cork stoppers (R).

The main advantage of the process of the invention is that the process can mimic the positional conditions of the stopper (R) inside a bottle neck (2) and in such a way obtain precise results that would not be possible otherwise.

In fact, the shape of a bottle neck (2), for example a normalized bottle neck, is not completely cylindrical. Actually, as can be seen in the schematic representations in FIGS. 3 and 4, the bottle neck (2) is approximately cylindrical at the "mouth" of the bottle, but its diameter increases slightly towards the interior of the bottle. On the other hand, also the shape of the stopper (R) may be not perfectly cylindrical, being in some cases conical or approximately conical. In this way, usually, the body of a cork stopper (R) is not entirely fitted in the bottle neck (2) after the corking process.

The skilled person knows that when a cork stopper (R) is inserted into a bottle neck (2), the part of the stopper (R) herein called the "central part" is perfectly adjusted to the wall of the bottle neck (2) and that the parts herein called "ends" of the stopper (R) could be slightly moved away from the wall of the bottle neck (2), mainly the end (5b) that lays inside the bottle.

In this circumstances, due to the radial compression of the cork stopper (R) in the corking process and due to said adhesion to the bottle neck (2), the central part (4) of the cork stopper body is in a sealing position with the bottle neck (2), meaning that any internal channel (3) that emerges m this central part (4) of the stopper (R) is hermetically sealed by the wall of the bottle neck, therefore not allowing fluid passage to the outside of the bottle and vice-versa.

This question is very relevant, as a process for checking out the sealing of a cork stopper (R) that would not consider this limitation could note sealing failures on the central part (4) of the stopper (R), and in this way would lead to the rejection of corks stoppers (R) that would be otherwise suitable to properly perform its function.

In this way, the fluid communication from and towards the outside of the bottle is limited to the presence of internal defects (3) (channels) that are communicating between the ends (5a, 5b) of the cork stopper body.

Accordingly, the process for checking out the sealing of cork stoppers (R) of the invention comprises the steps of:
a) dividing a cork stopper (R) in two ends (5a, 5b) and a central part (4);
b) hermetically sealing the central part (4) of the cork stopper (R) body in relation to the outside environment by means of an inflatable sleeve;
c) isolating the ends (5a, 5b) of the stopper (R) in compartments (8a, 8b);
d) closing at least one of said compartments (8a, 8b), such that the at least one compartment (8a, 8b) thus closed is hermetically isolated from the outside environment;
e) pressurizing said at least one compartment (8a, 8b) with a test fluid;
f) detecting a head loss in said at least one closed compartment (8a, 8b) or detecting the presence or absence of test fluid in the opposing compartment (8b, 8a).

In one embodiment of the process of the invention, in step d), both compartments (8a, 8b) are closed so as to hermetically isolate them from the outside environment.

In this latter case, step e) and step f) of pressurization and detection, respectively, can be carried out sequentially in both compartments (8a, 8b). In other words, steps e) and f) can be carried out alternately for each of the compartments (8a, 8b). Obviously, a simultaneous pressurization of both compartments (8a, 8b) should not be done, as such action does not allow the creation of a differential of pressure between the compartments (8a, 8b).

The operation parameters of the process are identical to those previously mentioned for the device (1) of the invention, whereby no further information is needed on such matter.

Tests

Tests have been carried out that demonstrated that several corks stoppers (R) considered suitable by processes of the prior art were not in fact appropriate for sealing of wine containers, whereas it was also shown that several discarded cork stoppers (R) had the needed sealing ability.

For example, tests carried out in stoppers made of colmated natural cork have surprisingly shown that the assumed sealing assigned to these stoppers was not always verified, in other words, several of these stoppers did not shown a sealing behaviour, which is totally unexpected.

Tests were also carried out in stoppers made of natural cork that had passed in visual inspection tests of the prior art and that had been selected as sealing stoppers (R). The tests with the process and device (1) of the present invention have shown that some of these cork stoppers (R) did not have the necessary sealing ability to be applied to wine bottles. These results were not unexpected, as according to the background of the invention section of this description, it was known that some of those stoppers (R) would not fulfil its sealing function, although was not obviously possible to determine which stoppers were in that situation.

It was further possible to check out that some natural cork stoppers, tested by the processes of the prior art and discarded, had is fact sealing ability and had been consequently wrongly discarded.

Therefore, the process and device (1) of the present invention allowed to individually determining in a precise way the appropriate cork stoppers from those defective, drastically increasing the yield and the effectiveness of the process of selection of cork stoppers (R).

The present invention differs totally from the prior art, as it provides a way of checking the actual sealing of each cork (R) tested, without using estimates or empirical evaluations yielding statistically acceptable results for batches of cork stoppers (R), but failing in terms of accuracy when it is intended to know individually the sealing ability of cork stoppers.

The invention claimed is:

1. A sealing test device for checking out the sealing of a cork stopper, which cork stopper comprises a body defining a central part and two ends, the device comprising:
a cork stopper receiving chamber;
a chamber partitioning mechanism which divides the chamber in two components, the mechanism comprising:
an adjustable insulator said central part of the cork stopper, wherein the insulator is configured for, upon actuation, sealing hermetically the central part of the cork stopper body in relation to the outside environment, and simultaneously for arranging each end of the cork stopper in one of said compartments,
an insulator actuation member, configured for, upon actuation, arranging the insulator on the central part of the cork stopper body;
at least one chamber compartment closing block arranged for, in operation, closing and hermetically isolating a respective compartment in relation to the outside environment and, together with said insulator, for isolating hermetically the compartments from each other;
at least one test fluid inlet arranged in at least one closing block;
at least one detection member arranged for detecting head loss or for defecting test fluid in at least one of the compartments; and
at least one test fluid source connected to at least one test fluid inlet.

2. The device according to claim 1, wherein the insulator is made of elastic and sealing material.

3. The device according to claim 2, wherein the insulator is an inflatable sleeve.

4. The device according to claim 1, wherein the insulator actuation member is a compressor.

5. The device according to claim 1, wherein the test fluid is a food grade gas.

6. The device according to claim 1, wherein the test fluid source is a compressor.

7. The device according to claim 1, wherein the detection member is a pressure gauge or a flowmeter.

8. The device according to claim 1, wherein the detection member is a manometer.

9. The device according to claim 1, comprising m inflatable sleeve made of elastic and sealing material; a compressor to inflate said inflatable sleeve; a test fluid inlet arranged in a closing block; a detection member connected to the closing block; and a compressor connected to the test fluid inlet.

10. The device according to claim 1, comprising a first closing block and a second closing block arranged for, in operation, closing and hermetically isolating the compartment and the compartment, respectively.

11. A sealing test process for checking out the sealing of a cork stopper, comprising steps of:
a) dividing the cork stopper in two ends and a central part;
b) hermetically sealing the central part of the cork stopper in relation to outside environment by means of an inflatable sleeve;
c) isolating the ends of the cork stopper in compartments;

d) closing at least one of said compartments, such that the at least one compartment thus closed is hermetically isolated from the outside environment;
e) pressurizing said at least one compartment with a test fluid;
f) detecting a head loss in said at least one closed compartment or detecting the presence or absence of the test fluid in the other compartment.

12. The process according to claim 11, wherein in step d) both compartments are closed so as to hermetically isolate them from the outside environment.

13. The process according to claim 12, wherein step e) and step f) are repeated alternately for each of the compartments.

14. The process according to claim 11, wherein in step a) of dividing the rink stopper, the central part has a size in the range of 5 to 30 mm.

15. The process according to claim 11, wherein step e) is carried out with a pressure in the range of 150 to 1000 mbar, for 0.4 to 10 seconds, preferably with a pressure of 900 mbar for 0.4 to 0.5 seconds.

* * * * *